(12) United States Patent
Doerr et al.

(10) Patent No.: US 9,517,348 B2
(45) Date of Patent: Dec. 13, 2016

(54) IMPLANTABLE CARDIAC THERAPY DEVICE

(75) Inventors: Thomas Doerr, Berlin (DE); Ingo Weiss, Berlin (DE)

(73) Assignee: BIOTRONIK SE & CO. KG, Berlin (DE)

( * ) Notice: Subject to any disclaimer, the term of this patent is extended or adjusted under 35 U.S.C. 154(b) by 983 days.

(21) Appl. No.: 13/597,262

(22) Filed: Aug. 29, 2012

(65) Prior Publication Data

US 2013/0066141 A1 Mar. 14, 2013

Related U.S. Application Data

(60) Provisional application No. 61/534,393, filed on Sep. 14, 2011.

(51) Int. Cl.
| | |
|---|---|
| A61N 1/365 | (2006.01) |
| A61N 1/362 | (2006.01) |
| A61N 1/368 | (2006.01) |
| A61M 1/12 | (2006.01) |

(Continued)

(52) U.S. Cl.
CPC ............ *A61N 1/3627* (2013.01); *A61M 1/122* (2014.02); *A61N 1/3684* (2013.01); *A61N 1/36521* (2013.01); *A61N 1/36564* (2013.01); *A61N 1/3712* (2013.01); *A61N 1/3962* (2013.01)

(58) Field of Classification Search
CPC .. A61N 1/3627; A61N 1/3684; A61N 1/3962; A61N 1/368; A61N 1/362; A61N 1/3622; A61N 1/08; A61N 1/36; A61N 1/36132; A61B 5/0205; A61B 5/0402; A61B 5/0452; A61B 5/0006; A61B 5/0215; A61B 5/6869; A61B 5/02; A61B 5/4836; A61B 5/04012; A61B 5/042; A61B 5/0031; A61B 5/04; A61B 5/046; A61B 5/0484; A61B 5/1107; A61B 5/486; A61M 1/122; A61M 1/12; A61M 1/1086; A61M 1/1053; A61M 1/1046; A61M 1/127; A61M 2039/1022; A61M 2230/04; A61M 5/1723; A61F 2/24

See application file for complete search history.

(56) References Cited

U.S. PATENT DOCUMENTS

| | | | |
|---|---|---|---|
| 7,229,402 B2 * | 6/2007 | Diaz ................... | A61M 1/1037 600/16 |
| 2006/0036127 A1 | 2/2006 | Delgado, III | |
| 2006/0167334 A1 | 7/2006 | Anstadt et al. | |

(Continued)

FOREIGN PATENT DOCUMENTS

WO 2010/132451 A2 11/2010

OTHER PUBLICATIONS

European Search Report dated Jan. 7, 2013, 9 pages.

*Primary Examiner* — Deborah Malamud
(74) *Attorney, Agent, or Firm* — ARC IP Law, PC; Joseph J. Mayo

(57) ABSTRACT

An implantable cardiac therapy device having a heart assist pump, a stimulation unit, and a control unit. The heart assist pump is designed to be connected to a ventricle of a heart and an associated artery, and is designed to pump blood from a particular ventricle into an associated artery, thereby supporting the particular ventricle. The stimulation unit is designed to electrically stimulate a heart contraction, and the control unit is designed to control the heart assist pump and the stimulation unit in such a way that the stimulation unit induces synchronized motions of cardiac contraction while the heart assist pump operates in a ventricle-supporting manner.

20 Claims, 4 Drawing Sheets

(51) Int. Cl.
  *A61N 1/39* (2006.01)
  *A61N 1/37* (2006.01)

(56) References Cited

U.S. PATENT DOCUMENTS

2011/0160788 A1    6/2011   Pate
2011/0178361 A1    7/2011   Yomtov

* cited by examiner

IMPLANTABLE CARDIAC THERAPY DEVICE

This application claims the benefit of U.S. Provisional Patent Application 61/534,393 filed on 14 Sep. 2011, the specification of which is hereby incorporated herein by reference.

BACKGROUND OF THE INVENTION

Field of the Invention

At least one embodiment of the invention relates to an implantable cardiac therapy device.

Description of the Related Art

Known implantable cardiac therapy devices include, for example, heart assist pumps which are designed to be connected to a ventricle of a heart and an associated artery, and are designed to pump blood from a particular ventricle into an associated artery, thereby supporting/relieving the particular ventricle. Ventricular assist devices (VAD) are already being implanted, in particular, to assist a severely limited ventricular pumping function. It is also known to use biventricular VAD pumps to provide adequate treatment for patients with right-ventricular and left-ventricular heart failure.

Other known implantable cardiac therapy devices include cardiac stimulators such as cardiac pacemakers or defibrillators/cardioverters comprising a stimulation unit for electrically stimulating a heart contraction. In particular, biventricular stimulators are already being implanted for cardiac resynchronization therapy (CRT), which can emit electrical stimulation pulses to a right ventricle of a heart and to a left ventricle of a heart in order to stimulate a contraction of the particular ventricle. Within the scope of cardiac resynchronization therapy, the stimulation pulses are delivered in such a way that contractions of both ventricles are coordinated with each other in a manner similar to that of a healthy heart.

A combination of a VAD pump with a pacemaker is described in US 2006/0036127 A1 [0042].

BRIEF SUMMARY OF THE INVENTION

The problem addressed by at least one embodiment of the invention is that of creating a cardiac therapy device that provides new therapeutic possibilities.

The present disclosure provides a combination therapy device for promoting reverse remodeling in patients with severely limited ventricular pumping function, which is a combination of a heart assist pump (also referred to as a ventricular assist pump or ventricular assist device (VAD)) and a cardiac stimulator with a stimulation unit, and comprises a control unit which is connected in a controlling manner to the heart assist pump and the stimulation unit and is designed to control the heart assist pump and the stimulation unit in a coordinated manner such that the stimulation unit induces synchronized motions of cardiac contraction while the heart assist pump operates in a ventricle-supporting manner.

The control unit therefore acts as a therapy coordination unit which coordinates the pumping function and the stimulation in such a way that ventricular pumping support is provided and the cardiac contraction motions are synchronized, thereby establishing a correlation between the VAD pumping function for myocardial "pressure and volume relief" and the electrically modulated contraction dynamics. The principle of combination therapy is to optimize the contraction processes and, especially, the valve closure mechanisms, in order to support reverse remodeling. In addition, the VAD flow can be reduced.

The disclosed implantable cardiac therapy device has the effect of improving reverse remodeling—that is, a reversal of the disease—in patients with greatly limited ventricular pumping function.

At least one embodiment of the disclosed implantable cardiac therapy device can increase the therapeutic efficiency of ventricular assist pumps, at least in some cases, such that the reverse remodeling that can be achieved is sufficient for stabilizing cardiac function even without a VAD system.

At least one embodiment of the invention incorporates the finding that ventricular assist pumps (VAD) are already being used successfully today for patients with severely limited ventricular pumping function and myocardial perfusion deficit, and that, in some cases, reverse remodeling was observed that was so successful that, after a VAD therapy phase, these patients can continue their lives without ever needing such a VAD system again.

These are only a few isolated incidents, however, and a concept has not existed for treating patients in large numbers so successfully that the use of VAD systems, which have many disadvantages, is needed for only a relatively short period of time. Less expensive VAD therapy would therefore also be possible.

at least one embodiment of the invention also incorporates the finding that current VAD systems are preferably pressure-controlled, and a disadvantage of this control is that cardiac resynchronization and, in part, AV synchronization of the cardiac cycle cannot be optimized. The therapeutic benefits of CRT therapy are therefore lost on these patients, and may potentially limit the reverse remodeling.

The same applies for biventricular VAD systems that in fact "relieve" both ventricles and therefore contribute to improved myocardial oxygen supply, but which are unable to eliminate an existing asymmetry of the contraction.

A further disadvantage of left-ventricular VAD systems that the inventors have recognized is that, although left-ventricular systolic discharge is increased when right-ventricular failure is also present, the volume load of the right ventricle increases simultaneously due to the venous return, thereby promoting right-ventricular heart failure.

The control unit serves as a therapy coordination unit which coordinates the pumping function and stimulation in such a way that ventricular pumping function is supported and cardiac contraction motions are synchronized, and as a contraction sequence control unit which controls the delivery and, if applicable, inhibition of stimulation pulses via the stimulation unit or even a plurality of stimulation units.

The control unit, in combination with the stimulation unit or a plurality of stimulation units, is preferably designed to control and induce the delivery of stimulation pulses for biventricular stimulation therapy.

As an alternative or in addition thereto, the control unit, in combination with the stimulation unit or a plurality of stimulation units, is designed to control and induce the delivery of stimulation pulses to an atrium or one or two ventricles.

The control unit, in combination with the stimulation unit or a plurality of stimulation units, is preferably designed to control stimulation therapy in such a way that it synchronizes the ventricle not connected to the assist pump with the pumping function in such a way that synchronous ventricular function is achieved. In particular, the control unit is designed to bring about an adequate delay between the point in time of the intended delivery of a right-ventricular stimulation pulse and the action of the left-ventricular heart assist pump.

According to a preferred variant embodiment, all or some of the stimulation electrodes are an integral component of the heart assist pump or one of its components, such as pump housing, supply lines, etc.

The implantable cardiac therapy device preferably comprises an impedance sensor for detecting intracardiac impedance, and a cardiac stimulator, or at least one stimulation unit that is controlled by the control unit, which are connected to the control unit. The control unit can be designed to control a delivery of stimulation pulses as a function of an output signal of the impedance sensor that indicates intracardiac impedance. In particular, the control unit—in combination with the impedance sensor and the stimulation unit—can be designed to control the stimulation on the basis of an output signal of the impedance sensor that indicates cardiac contractility in such a way that contractility is increased as needed. As a result, a combination therapy device having a CCM (Cardiac Contractility Modulation) stimulator is obtained for increasing contractility as needed.

As an alternative or in addition thereto, the implantable cardiac therapy device may include a defibrillation unit.

The implantable cardiac therapy device preferably comprises a pressure sensor as part of the heart assist pump and is designed to detect a mitral valve closure using the pressure sensor, and to control therapy times as a function of a mitral valve closure that was detected.

In respect to the control of the stimulation unit or stimulation units in terms of the points in time at which stimulation pulses are delivered, if applicable, the control unit can be designed as a contraction sequence control unit and perform closed-loop stimulation (CLS) which is known per se and is based on an evaluation of the right-ventricular contraction dynamics which are detected via one or more intracardiac impedance measurements using an appropriate impedance sensor.

The control of the delivery of stimulation pulses by the control unit in the sense of a contraction sequence control unit can be based on one or more measurements using a hemodynamic sensor (HDS).

The control unit, as a contraction sequence control unit, can also be designed to monitor stimulation success automatically in a manner known per se. In addition, the control unit can also be designed to automatically detect—on the basis of one or more monitorings of stimulation success—the stimulation threshold of the particular ventricle, and to automatically set the particular intensity of the stimulation pulse.

According to a particularly preferred variant embodiment, the implantable cardiac therapy device is equipped with a left-ventricular heart assist pump and sensing and stimulation units connected to the control unit including a sensor for detecting the right-ventricular contractility or contraction velocity, and is designed to lower the systolic discharge using the heart assist pump and, optionally, the stimulation frequency if the right-ventricular contractility decreases, in order to prevent right-ventricular volume overload.

Moreover, any combination of monoventricular and biventricular heart assist pumps (VAD pumps) with known systems for cardiac electrotherapy may be utilized with embodiments of the invention.

Furthermore a method for treating cardiac insufficiency is disclosed, comprising the steps of providing a heart assist pump which is designed to be connected to a ventricle of a heart and an associated artery, and is designed to pump blood from a particular ventricle into an associated artery, thereby supporting/relieving the particular ventricle, providing a stimulation unit for the electrical stimulation of a heart contraction, and providing a control unit which is connected in a controlling manner to the heart assist pump and the stimulation unit and is designed to control the heart assist pump and the stimulation unit in a coordinated manner such that the stimulation unit induces synchronized motions of cardiac contraction while the heart assist pump operates in a ventricle-supporting manner.

The method can be exploited with the cardiac therapy devices described above, especially it can benefit from the different embodiments described above.

BRIEF DESCRIPTION OF THE DRAWINGS

The invention will now be explained in greater detail with reference to embodiments and the figures. They show, in.

DETAILED DESCRIPTION OF THE INVENTION

Figure 1:
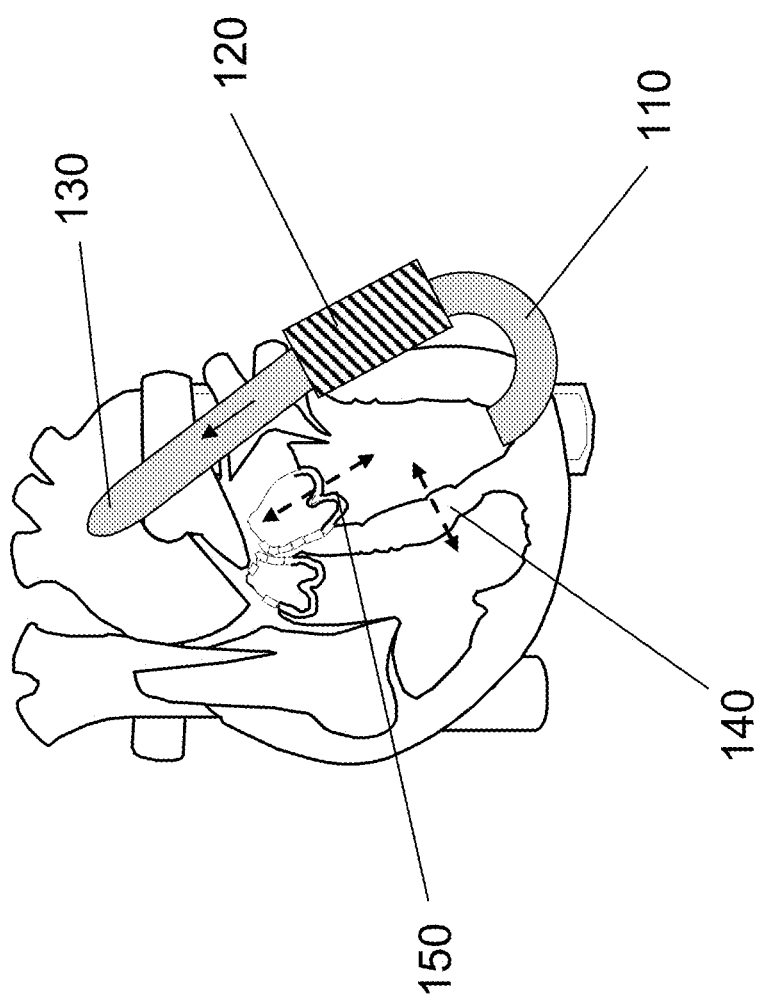
FIG. 1: a heart assist system (VAD system) according to the prior art.

FIG. 1 shows the state of the art of a VAD system. A supply line (110) is implanted in the left ventricle of the patient for connection of the assist pump (120). The purpose of this supply line is to allow a portion of the blood to flow from the left ventricle to the pump (120). The assist pump, in turn, pumps the blood volume into the aorta (130) and thereby relieves the left ventricle, thereby overcompensating for the myocardial oxygen deficit and promoting reverse remodeling.

These systems are typically pressure-controlled, however, and do not provide any additional methods for the resynchronization of the remaining mechanics of the heart. The disruptions of the cardiac mechanics that are typical of pronounced heart failure, interventricular dyssynchrony (140) and atrioventricular dyssynchrony (150), continue to exist in the patients. Due to these functional disturbances of movements, it can be assumed that curative therapy with reverse remodeling is hindered to a notable extent.

Figure 2:
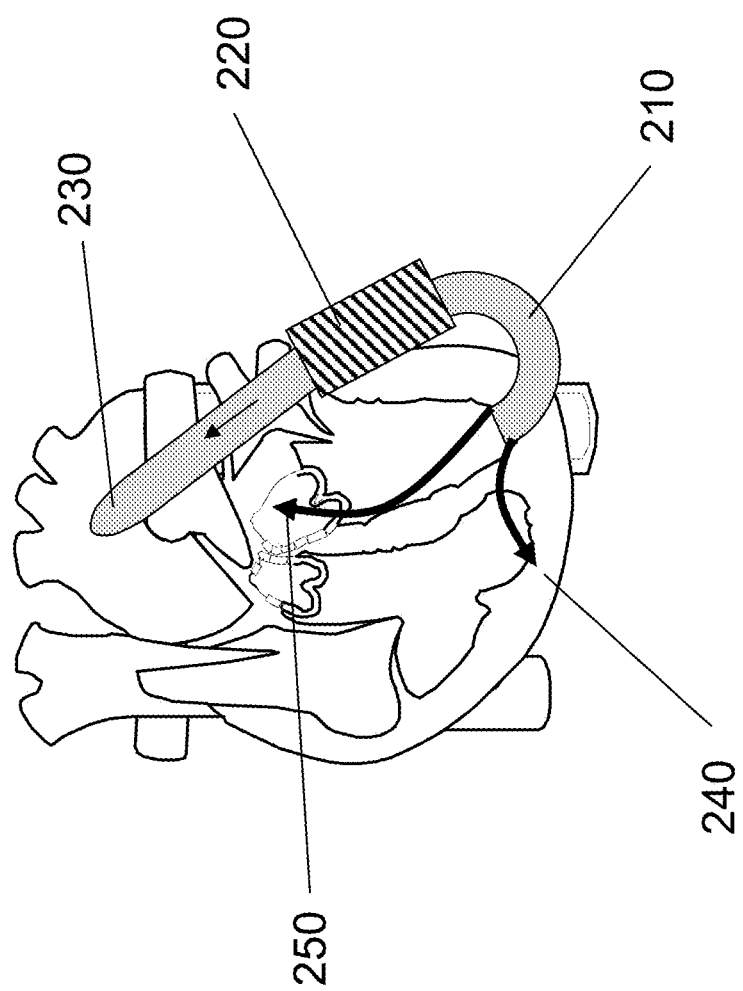
FIG. 2: a heart assist system having electrical ventricular synchronization.

The system according to an embodiment of the invention is depicted in FIG. 2. In this case, the VAD pump (220) with its supply line (210) and discharge line (230) also includes a right-ventricular electrode lead (240) and a left-atrial electrode lead (250) as integral components of the VAD system.

The left-atrial electrode lead is used primarily to sense left-atrial stimulation, and the right-ventricular electrode lead is used to stimulate the right ventricle.

The mode of operation is explained in the block diagram and flow chart that follow.

Figure 3:
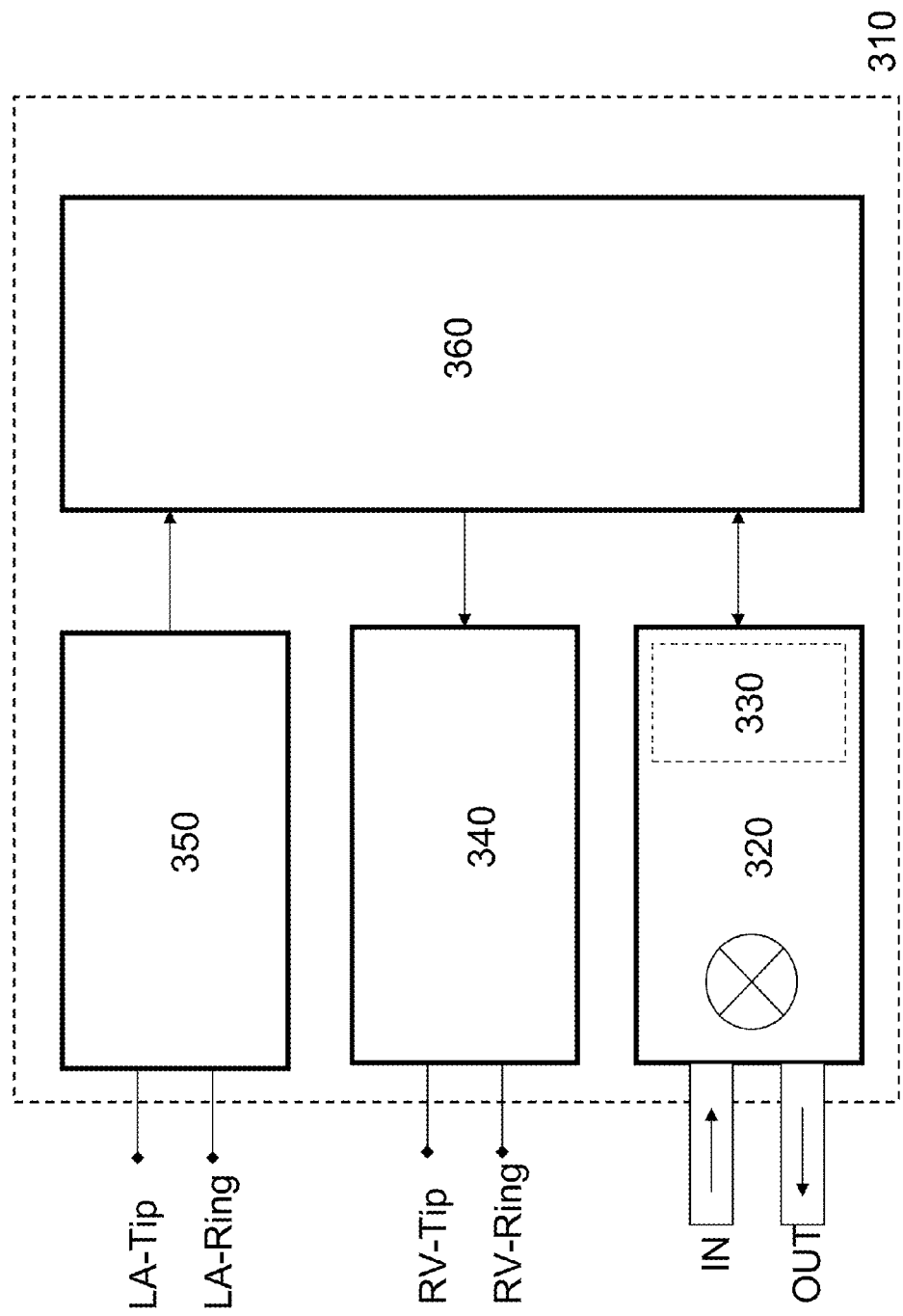
FIG. 3: a block diagram of the heart assist system with integrated resynchronization device.

The block diagram of the VAD system (310) with integrated resynchronization device is depicted in FIG. 3. It includes the actual heart assist pump (320) for assisting the left ventricle, which usually includes a pressure sensor system (330) comprising a pressure sensor for the control thereof, and is connected to the left-ventricular supply line (IN) and the aortal discharge line (OUT). This system also includes a right-ventricular stimulation and contraction sequence control unit (340), which is connected to a bipolar right-ventricular stimulation electrode (RV Tip, RV Ring). A left-atrial sensing unit (350), which is connected to the bipolar left-atrial sensing electrode (LA Tip, LA Ring), is also integrated therein. All of the aforementioned units are connected to a therapy synchronization unit (360), the mode of operation of which is described with reference to FIG. 4.

Figure 4:
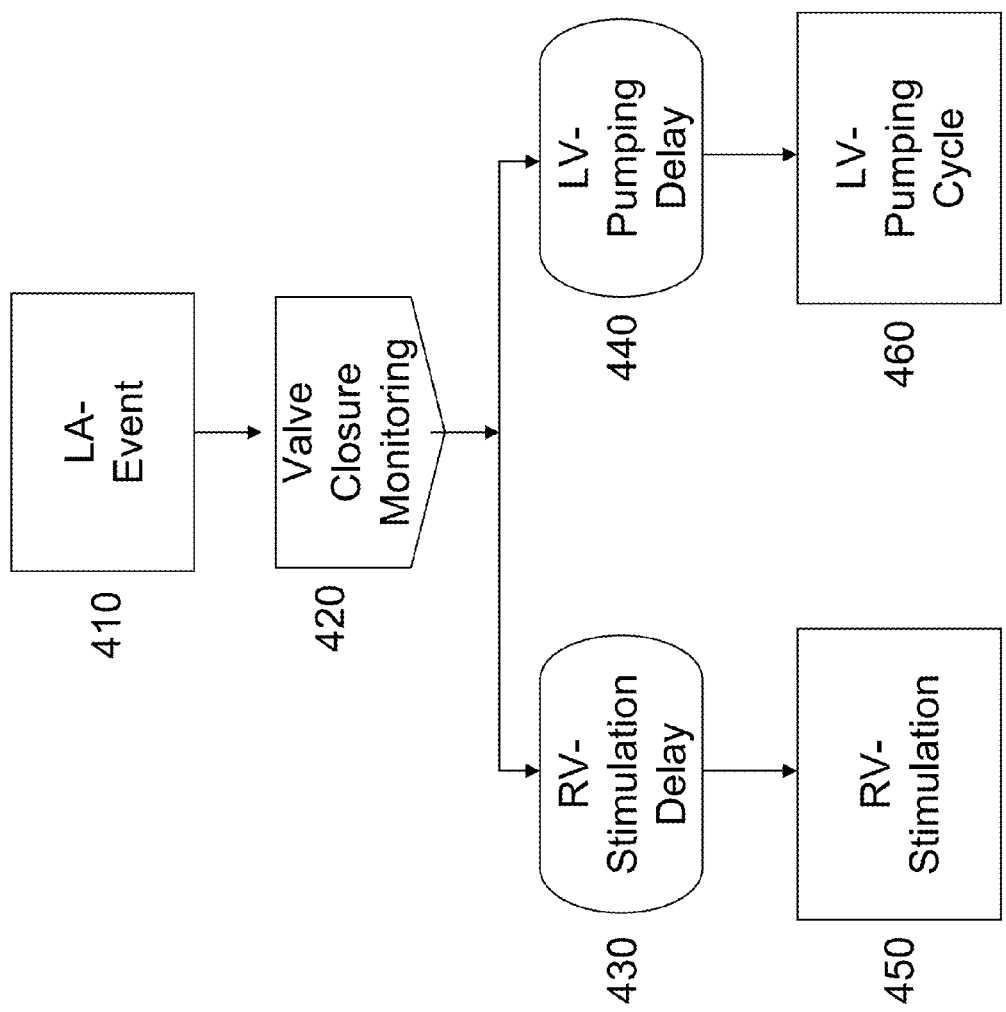
FIG. 4: a flow chart that depicts the mode of operation of the therapy synchronization unit.

The mode of operation of the control unit as therapy synchronization unit is depicted in FIG. 4. First, a left-atrial sensing (410) prompts monitoring of the mitral valve closure (420) using the existing VAD pressure sensor system, i.e. the first step is to wait for the mitral valve to close. Next, two delay times (430) and (440), which can be programmed independently of one another, are started simultaneously, in order to determine the point in time for the right-ventricular stimulation (450) and left-ventricular pumping activity (460) that are optimal for resynchronization. In addition, the course of right-ventricular contraction and the contraction dynamics are detected and used to dynamically adapt the programmable delay times to the resynchronization needs and, optionally, to reduce the heart rate and LV pumping output if the RV contractility is no longer able to follow the LV systolic discharge. Right-ventricular heart failure is thereby prevented.

A feature of at least one embodiment of the invention is, that it has the potential to increase the therapeutic efficiency of VAD therapy to a notable extent, and to thereby promote sustained reverse remodeling in order to wean VAD patients from the VAD system.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

What is claimed is:

1. An implantable cardiac therapy device comprising
a heart assist pump which is configured to connect to a particular ventricle of a heart and an associated artery, and configured to pump blood from the particular ventricle into the associated artery, to support or relieve the particular ventricle;
a stimulation unit configured to electrically stimulate a heart contraction; and,
a control unit which is connected to the heart assist pump and the stimulation unit and configured to control the heart assist pump and the stimulation unit in a coordinated manner such that
the stimulation unit induces synchronized motions of cardiac contraction while the heart assist pump operates in a ventricle-supporting manner;
said stimulation unit comprises at least one stimulation unit and said control unit, in combination with the at least one stimulation unit or a plurality of stimulation units, is configured to control stimulation therapy to synchronize a ventricle not connected to the heart assist pump with pumping function of the heart assist pump to achieve synchronous ventricular function;
said control unit is configured to utilize a delay between a point in time of an intended delivery of a right-ventricular stimulation pulse and an action of the heart assist pump coupled with a left ventricle of the heart, said action of the heart assist pump coupled with a left ventricle of the heart comprises left-ventricular pumping activity, and,
said delay time comprises two delay times and said control unit is further configured to detect a course of right-ventricular contraction and contraction dynamics and to dynamically adapt the two delay times to resynchronization needs.

2. The implantable cardiac therapy device according to claim 1, wherein the control unit is configured, in combination with the stimulation unit, to deliver stimulation pulses to both ventricles of the heart in a coordinated manner.

3. The implantable cardiac therapy device according to claim 1, wherein said stimulation unit comprises at least one stimulation unit and wherein the control unit, in combination with the at least one stimulation unit, is configured to control and induce delivery of stimulation pulses to achieve biventricular stimulation therapy.

4. The implantable cardiac therapy device according to claim 1, wherein said stimulation unit comprises at least one stimulation unit and wherein the control unit, in combination with the at least one stimulation unit, is configured to control and induce delivery of stimulation pulses to an atrium and one or two ventricles.

5. The implantable cardiac therapy device according to claim 1, further comprising stimulation electrodes, wherein the stimulation unit is connected to the stimulation electrodes, some or all of which are an integral component of the heart assist pump or a portion thereof.

6. The implantable cardiac therapy device according to claim 1, further comprising a pressure sensor as part of the heart assist pump wherein the pressure sensor is configured to detect a mitral valve closure, and wherein the control unit is configured to control therapy times as a function of the mitral valve closure that was detected.

7. The implantable cardiac therapy device according to claim 1, further comprising an impedance sensor and wherein said stimulation unit comprises at least one stimulation unit and wherein the control unit is configured to function as a contraction sequence control unit that is configured to control the at least one stimulation unit with respect to points in time at which stimulation pulses are delivered, and if applicable, is configured to perform closed-loop stimulation or CLS which is based on an evaluation of right-ventricular contraction dynamics which are detected via one or more intracardiac impedance measurements obtained from said impedance sensor.

8. The implantable cardiac therapy device according to claim 1, wherein the control unit is configured to function as a contraction sequence control unit, that is configured to automatically monitor stimulation success.

9. The implantable cardiac therapy device according to claim 8, wherein the control unit is configured to automatically detect a stimulation threshold of a ventricle, and to automatically set a particular intensity of a stimulation pulse based on said stimulation success.

10. The implantable cardiac therapy device according to claim 1, wherein said heart assist pump is configured as a left-ventricular heart assist pump and further comprising sensing and stimulation units connected to the control unit including a sensor connected to the control unit that is configured to detect right-ventricular contractility or contraction velocity, and wherein the control unit is configured to lower systolic discharge via the heart assist pump and, optionally, lower stimulation frequency if the right-ventricular contractility decreases, in order to prevent right-ventricular volume overload.

11. The implantable cardiac therapy device according to claim 1, further comprising an impedance sensor configured to detect intracardiac impedance, and a cardiac stimulator, or at least one stimulation unit which is connect to and controlled by the control unit, wherein the control unit is configured to control delivery of stimulation pulses as a function of an output signal of the impedance sensor, which indicates intracardiac impedance.

12. The implantable cardiac therapy device according to claim 11, wherein the control unit is configured to control delivery of stimulation pulses based on the output signal of the impedance sensor that indicates cardiac contractility to increase contractility as needed.

13. The implantable cardiac therapy device according to claim 1, further comprising a defibrillation unit which is configured to generate and deliver defibrillation pulses, and which is connected to and controlled by the control unit.

14. The implantable cardiac therapy device according to claim 1, wherein said two delay times are started simultaneously.

15. A method for treating cardiac insufficiency with an implantable cardiac therapy device comprising:
    pumping blood from a particular ventricle into an associated artery of a heart, to support or relieve the particular ventricle with a heart assist pump which is configured to connect to the particular ventricle of the heart and the associated artery;
    stimulating a heart contraction electrically with a stimulation unit,
        wherein said stimulation unit comprises at least one stimulation unit;
    controlling the heart assist pump and the stimulation unit in a coordinated manner with a control unit which is connected to the heart assist pump and the stimulation unit and wherein said controlling further comprises
        inducing synchronized motions of cardiac contraction with the stimulation unit while operating the heart assist pump in a ventricle-supporting manner;
    controlling stimulation therapy to synchronize a ventricle not connected to the heart assist pump with pumping function of the heart assist pump to achieve synchronous ventricular function with the control unit in combination with the at least one stimulation unit or a plurality of stimulation units;
    utilizing a delay between a point in time of an intended delivery of a right-ventricular stimulation pulse and an action of the heart assist pump coupled with a left ventricle of the heart with the control unit, wherein the action of the heart assist pump coupled with a left ventricle of the heart comprises left-ventricular pumping activity, and,
    wherein said delay time comprises two delay times and wherein the control unit is further configured to detect a course of right-ventricular contraction and contraction dynamics and to dynamically adapt the two delay times to resynchronization needs.

16. The implantable cardiac therapy device according to claim 1, wherein said two delay times are configured to be programmed independently of one another, and wherein said two delay times are started independently to determine the point in time of an intended delivery of a right-ventricular stimulation pulse with the control unit.

17. The method for treating cardiac insufficiency with an implantable cardiac therapy device according to claim 15, wherein said two delay times are programmed independently of one another, and further comprising starting said two delay times independently to determine the point in time of an intended delivery of a right-ventricular stimulation pulse with the control unit.

18. The method for treating cardiac insufficiency with an implantable cardiac therapy device according to claim 15, wherein said two delay times are started simultaneously.

19. An implantable cardiac therapy device comprising
    a heart assist pump which is configured to connect to a particular ventricle of a heart and an associated artery, and configured to pump blood from the particular ventricle into the associated artery, to support or relieve the particular ventricle;
    a stimulation unit configured to electrically stimulate a heart contraction; and,
    a control unit which is connected to the heart assist pump and the stimulation unit and configured to control the heart assist pump and the stimulation unit in a coordinated manner such that
        the stimulation unit induces synchronized motions of cardiac contraction while the heart assist pump operates in a ventricle-supporting manner;
    said stimulation unit comprises at least one stimulation unit and said control unit, in combination with the at least one stimulation unit or a plurality of stimulation units, is configured to control stimulation therapy to synchronize a ventricle not connected to the heart assist pump with pumping function of the heart assist pump to achieve synchronous ventricular function,
    said control unit is configured to utilize a delay between a point in time of an intended delivery of a right-ventricular stimulation pulse and an action of the heart assist pump coupled with a left ventricle of the heart, said action of the heart assist pump coupled with a left ventricle of the heart comprises left-ventricular pumping activity, and,
    said delay time comprises two delay times configured to be programmed independently of one another, and said two delay times are started independently to determine the point in time of an intended delivery of a right-ventricular stimulation pulse with the control unit.

20. A method for treating cardiac insufficiency with an implantable cardiac therapy device comprising:
    pumping blood from a particular ventricle into an associated artery of a heart, to support or relieve the particular ventricle with a heart assist pump which is configured to connect to the particular ventricle of the heart and the associated artery;
    stimulating a heart contraction electrically with a stimulation unit,
        wherein said stimulation unit comprises at least one stimulation unit;
    controlling the heart assist pump and the stimulation unit in a coordinated manner with a control unit which is connected to the heart assist pump and the stimulation unit and wherein said controlling further comprises
        inducing synchronized motions of cardiac contraction with the stimulation unit while operating the heart assist pump in a ventricle-supporting manner;
    controlling stimulation therapy to synchronize a ventricle not connected to the heart assist pump with pumping function of the heart assist pump to achieve synchronous ventricular function with the control unit in combination with the at least one stimulation unit or a plurality of stimulation units;
    utilizing a delay between a point in time of an intended delivery of a right-ventricular stimulation pulse and an action of the heart assist pump coupled with a left ventricle of the heart with the control unit, wherein the action of the heart assist pump coupled with a left ventricle of the heart comprises left-ventricular pumping activity, and, wherein said delay time comprises two delay times that are programmed independently of one another, and further comprising starting said two delay times independently to determine the point in time of an intended delivery of a right-ventricular stimulation pulse with the control unit.

* * * * *